(12) United States Patent
Goto et al.

(10) Patent No.: US 10,905,860 B2
(45) Date of Patent: Feb. 2, 2021

(54) VASCULAR OCCLUSION BALLOON CATHETER

(71) Applicant: TERUMO CLINICAL SUPPLY CO., LTD., Kakamigahara (JP)

(72) Inventors: Kazumi Goto, Gifu (JP); Tatsuya Kawase, Ichinomiya (JP); Nozomi Nakanishi, Kakamigahara (JP); Sayumi Hirose, Gifu (JP)

(73) Assignee: TERUMO CLINICAL SUPPLY CO., LTD., Kakamigahara (JP)

( * ) Notice: Subject to any disclaimer, the term of this patent is extended or adjusted under 35 U.S.C. 154(b) by 852 days.

(21) Appl. No.: 15/468,592

(22) Filed: Mar. 24, 2017

(65) Prior Publication Data

US 2017/0274188 A1   Sep. 28, 2017

(30) Foreign Application Priority Data

Mar. 25, 2016   (JP) ................................ 2016-062215

(51) Int. Cl.
*A61M 25/10* (2013.01)
*A61B 17/12* (2006.01)
(Continued)

(52) U.S. Cl.
CPC ......... *A61M 25/10* (2013.01); *A61B 17/1204* (2013.01); *A61B 17/12109* (2013.01);
(Continued)

(58) Field of Classification Search
CPC .. A61M 2025/1077; A61M 2005/3123; A61M 5/36; A61M 25/10
See application file for complete search history.

(56) References Cited

U.S. PATENT DOCUMENTS 4,638,805 A * 1/1987 Powell .................. A61M 25/10
606/192
4,821,722 A 4/1989 Miller et al.
(Continued)

FOREIGN PATENT DOCUMENTS

| EP | 0 284 672 A1 | 10/1988 |
| EP | 0 356 748 A2 | 3/1990 |
| JP | 2005-103120 A | 4/2005 |

OTHER PUBLICATIONS

The extended European Search Report dated Aug. 24, 2017, by the European Patent Office in corresponding European Patent Application No. 17162665.8-1501 (7 pages).

*Primary Examiner* — Jenna Zhang
(74) *Attorney, Agent, or Firm* — Buchanan Ingersoll & Rooney PC

(57) ABSTRACT

The vascular occlusion balloon catheter has a balloon, a main lumen, and a balloon expanding lumen. The balloon catheter has an air discharge passage. The air discharge passage has a distal end opening located at a position distal from the balloon and a proximal end communicating with an inner portion of the balloon. The distal end opening of the air discharge passage is positioned inside a portion disposed proximally from a distal end of the balloon catheter. The air discharge passage communicates with the main lumen at the distal end opening of the air discharge passage. The area of a cross section of the air discharge passage orthogonal to an axial direction of the balloon catheter is set to 200 µm² to 450 µm². The length of the air discharge passage is set to 1.0 to 3.0 mm.

17 Claims, 9 Drawing Sheets

(51) Int. Cl.
*A61M 25/01* (2006.01)
*A61M 5/36* (2006.01)
*A61M 25/00* (2006.01)

(52) U.S. Cl.
CPC ......... *A61B 17/12136* (2013.01); *A61M 5/36* (2013.01); *A61M 25/0102* (2013.01); *A61M 25/104* (2013.01); *A61M 25/005* (2013.01); *A61M 25/1006* (2013.01); *A61M 2025/1052* (2013.01); *A61M 2025/1077* (2013.01); *A61M 2025/1079* (2013.01); *A61M 2025/1081* (2013.01)

(56) References Cited

U.S. PATENT DOCUMENTS

| | | | | |
|---|---|---|---|---|
| 4,921,483 | A | * | 5/1990 | Wijay .............. A61M 25/1002 604/103.1 |
| 4,938,220 | A | * | 7/1990 | Mueller, Jr. ............ A61B 6/12 600/435 |
| 5,049,130 | A | * | 9/1991 | Powell .................. A61B 8/445 604/103.05 |
| 5,135,486 | A | * | 8/1992 | Eberle ................ A61M 25/104 604/103.1 |
| 5,256,143 | A | * | 10/1993 | Miller .................. A61M 29/02 604/102.02 |
| RE34,564 | E | | 3/1994 | Mar et al. |
| 5,449,343 | A | | 9/1995 | Samson et al. |
| 5,558,643 | A | | 9/1996 | Samson et al. |
| 2010/0010442 | A1 | * | 1/2010 | Shivkumar .......... A61M 39/10 604/122 |
| 2017/0165435 | A1 | * | 6/2017 | Green .................... A61M 5/36 |

\* cited by examiner

VASCULAR OCCLUSION BALLOON CATHETER

BACKGROUND OF THE INVENTION

Field of the Invention

The present invention relates to a vascular occlusion balloon catheter to be inserted into a blood vessel.

Description of the Related Art

The vascular occlusion balloon catheter is used to perform angiography, inject a liquid medicine such as a chemotherapeutic agent into blood vessel, and perform vascular embolization.

The balloon catheter disclosed in U.S. Pat. No. 4,638,805 [Japanese Examined Patent Application Publication No. 03(1991)-56067] (Patent document 1) has the apparatus for discharging air from the inside of the balloon and restraining the liquid from escaping from the balloon. As the apparatus for discharging the air from the inside of the balloon and restraining the liquid from escaping from the balloon, there is disclosed the very small passage 21 extended from the inside of the balloon to the periphery of the distal end of the balloon catheter 11. According to the disclosure, the wire used to form the small passage has the diameter not more than 0.001 inches (0.0254 mm), for example, 0.0005 inches (0.0127 mm). The wire having the diameter of 0.001 inches (0.0254 mm) has the sectional area of about 506 $\mu m^2$. The wire having the diameter of 0.0005 inches (0.0127 mm) has the sectional area of about 126 $\mu m^2$.

The present applicant proposed the balloon catheter as disclosed in Japanese Patent Application Laid-Open Publication No. 2005-103120 (Patent document 2).

The balloon catheter of the patent document 2 is used after the priming operation (air inside balloon and balloon lumen is replaced with liquid) is performed by using the liquid containing the imaging agent for the balloon and the balloon lumen.

The balloon catheter 1 of the patent document 2 has the double tube-structured catheter body 3 having the inner tube 9 and the outer tube 21. The balloon 7 is mounted on the catheter body at its distal end portion. The injection liquid passage 23 formed between the inner tube and the outer tube communicates with the inside of the balloon through the distal end opening 22 of the outer tube. The purging hole 24 formed on the outer tube is closed with the purging hole cover 33. In purging air inside the balloon and the lumen, the purging hole cover is elastically displaced outward in the radial direction of the catheter to discharge the air and prevents the air from flowing in the opposite direction.

Because each of the balloon catheters of the patent documents 1 and 2 has the purging hole as described above, the priming operation can be accomplished. But in each of the balloon catheters of the patent documents 1 and 2, it takes time to perform the priming operation. In addition, although the priming operation may be easily performed, the liquid injected into the balloon flows out during the use of the balloon catheters, which leads to defective maintenance of the embolized state of a blood vessel.

Therefore, it is an object of the present invention to provide a vascular occlusion balloon catheter having a balloon which can be expanded by a liquid injected therein to and an air discharge passage which communicates with an inside of the balloon catheter and has is open at a distal end portion of the balloon catheter intended to allow a priming operation of replacing air inside the balloon with a liquid to be reliably and satisfactorily performed, allow a liquid injected into the balloon to flow out in a small amount from the balloon when the balloon catheter is used, and allow the balloon to keep a blood vessel-occluded state for a predetermined period of time.

SUMMARY OF THE INVENTION

The object described above is attained by a vascular occlusion balloon catheter comprising a vascular occlusion balloon and a shaft part having a main lumen and a balloon expanding lumen, wherein said vascular occlusion balloon catheter has an air discharge passage, said air discharge passage has a distal end opening located at a position distal from said vascular occlusion balloon and a proximal end communicating with an inner portion of said vascular occlusion balloon, said distal end opening of said air discharge passage is positioned inside a portion disposed proximally from a distal end of said vascular occlusion balloon catheter, said air discharge passage communicates with said main lumen at said distal end opening of said air discharge passage, and an area of a cross section of said air discharge passage orthogonal to an axial direction of said vascular occlusion balloon catheter is set to 200 $\mu m^2$ to 450 $\mu m^2$, and a length of said air discharge passage is set to 1.0 to 3.0 mm.

PREFERRED EMBODIMENTS OF THE INVENTION

Figure 1:
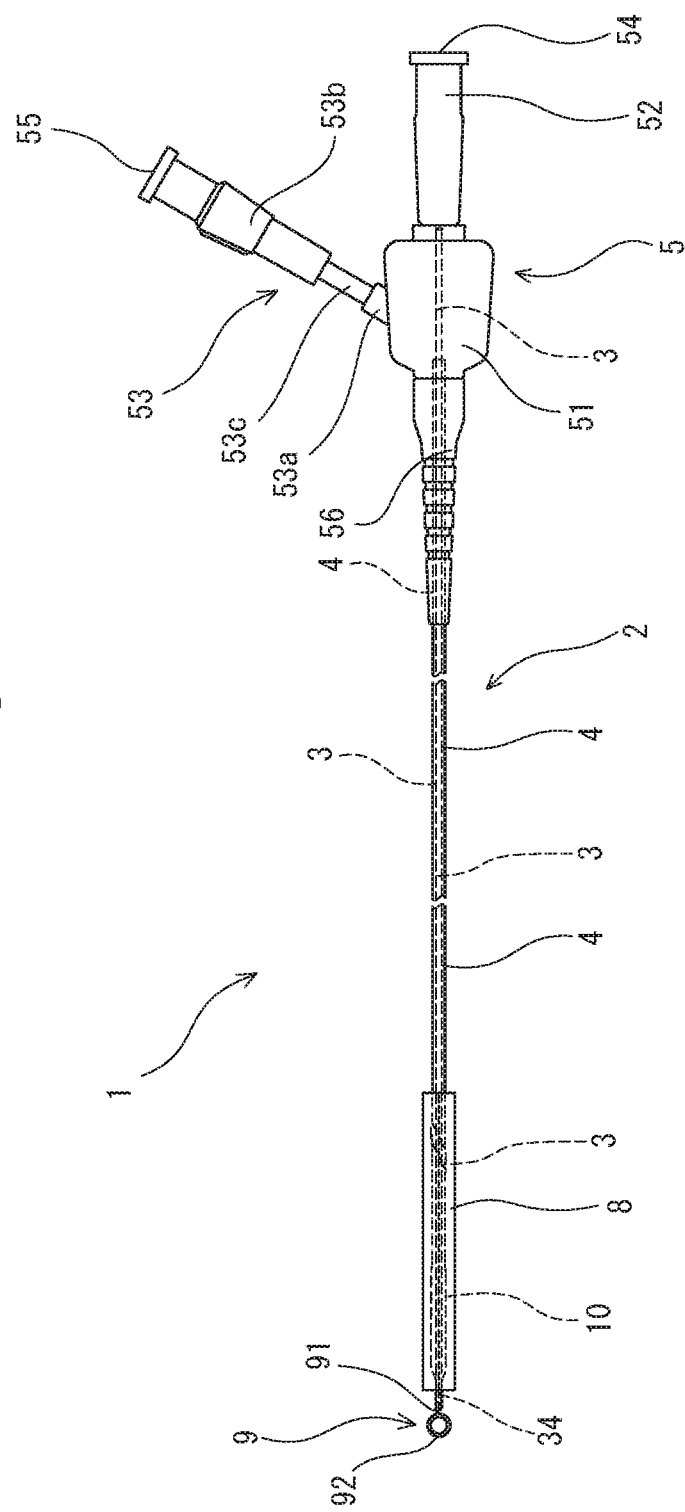
FIG. 1 is a partly abbreviated outside view of one embodiment of a balloon catheter assembly using a vascular occlusion balloon catheter of the present invention.

The vascular occlusion balloon catheter of the present invention is described below by using embodiments shown in the drawings.

A vascular occlusion balloon catheter (hereinafter referred to as balloon catheter) 2 of the present invention has a vascular occlusion balloon (hereinafter referred to as balloon) 10 elastically deformable and a shaft part having a main lumen 21 and a balloon expanding lumen 22. The vascular occlusion balloon catheter 2 has an air discharge passage 7. The air discharge passage 7 has a distal end (distal end opening 71) located at a position distal from the balloon 10 of the balloon catheter 2 and a proximal end communicates with an inner portion of the balloon 10. The distal end opening 71 of the air discharge passage 7 is positioned inside a portion disposed proximally from the distal end of the balloon catheter 2. As described above, the air discharge passage 7 communicates with the main lumen 21 at its distal end opening 71. The area of a cross section of the air discharge passage 7 orthogonal to an axial direction of the balloon catheter 2 is set to 200 µm² to 450 µm². The length of the air discharge passage 7 is set to 1.0 to 3.0 mm.

According to the vascular occlusion balloon catheter of the present invention, the area of the cross section of the air discharge passage orthogonal to the axial direction of the balloon catheter is set to 200 µm² to 450 µm². The length of the air discharge passage is set to 1.0 to 3.0 mm. The air discharge passage having the above-described form allows the priming operation of replacing the air inside the balloon with the liquid to be reliably and satisfactorily performed and the liquid injected into the balloon to flow out in a small amount after the priming operation finishes. The distal end opening of the air discharge passage is positioned inside the portion disposed proximally from the distal end of the balloon catheter. The liquid inside the balloon flows out in a small mount because a medical liquid such as an imaging agent, a medical agent, and the like injected into the main lumen when the balloon catheter is used is obstructive to the flow-out of the liquid from the balloon. Therefore, the balloon is capable of keeping the blood vessel-occluded state for a predetermined period of time.

By using a vascular occlusion balloon catheter assembly (hereinafter referred to as balloon catheter assembly) of the embodiment shown in the drawings, the balloon for use in the catheter of the present invention is described below.

Figure 2:
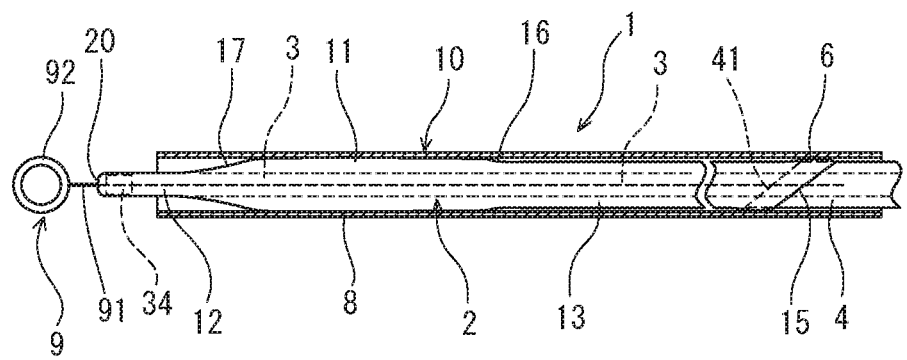
FIG. 2 is a partly cutaway enlarged outside view of a front side part of the balloon catheter assembly shown in FIG. 1.
Figure 3:
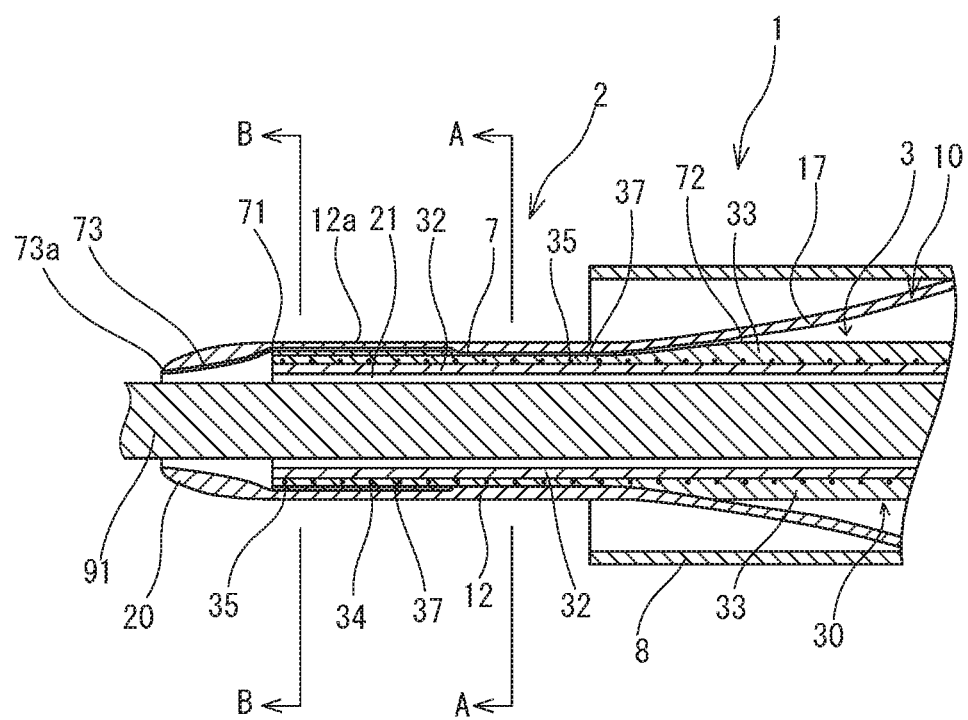
FIG. 3 is an enlarged sectional view of a distal end portion of the balloon catheter assembly shown in FIG. 1.

As shown in FIGS. 1 through 3, a balloon catheter assembly 1 of this embodiment has the balloon catheter 2, a sleeve 8 covering the balloon 10 and restraining the balloon 10 from expanding, and a mandrel 9 entering the balloon catheter 2 from the distal end opening thereof, passing a position of the distal end opening 71 of the air discharge passage 7, and entering into the main lumen 21.

As shown in FIGS. 4 through 13, the balloon catheter 2 has the shaft part and the balloon 10. The shaft part has an inner tube 3, an outer tube 4, and a hub 5.

More specifically, the balloon catheter 2 of this embodiment has the inner tube 3 having the main lumen 21, the outer tube 4 coaxial with the inner tube 3, having its distal end at a position rearward at a predetermined length from a distal end of the inner tube 3, and forming the balloon expanding lumen 22 between an outer surface of the inner tube 3 and the outer tube 4, and the expandable balloon 10 which has a distal side tubular part 12 fixed to the inner tube 3 and a proximal side tubular part 13 fixed to the outer tube 4, the inside of which communicates with the balloon expanding lumen 22.

Figure 4:
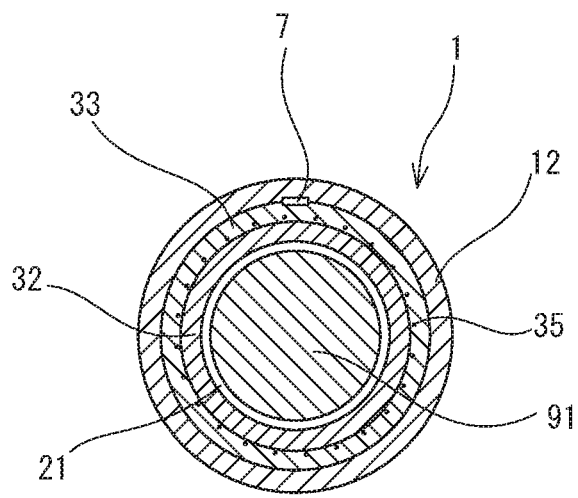
FIG. 4 is an enlarged sectional view taken along a line A-A of FIG. 3.
Figure 5:
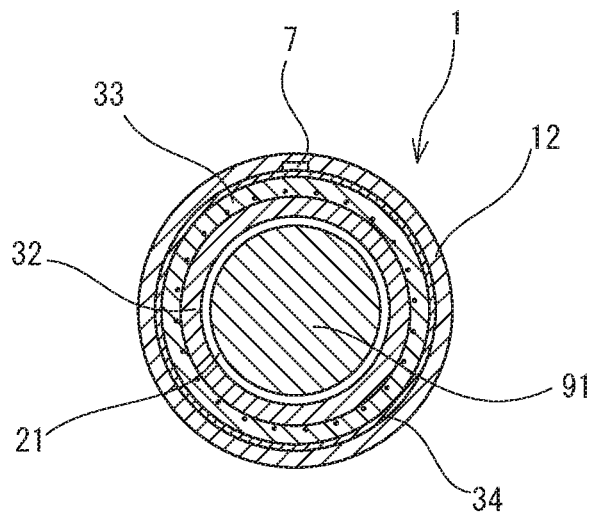
FIG. 5 is an enlarged sectional view taken along a line B-B of FIG. 3.
Figure 6:
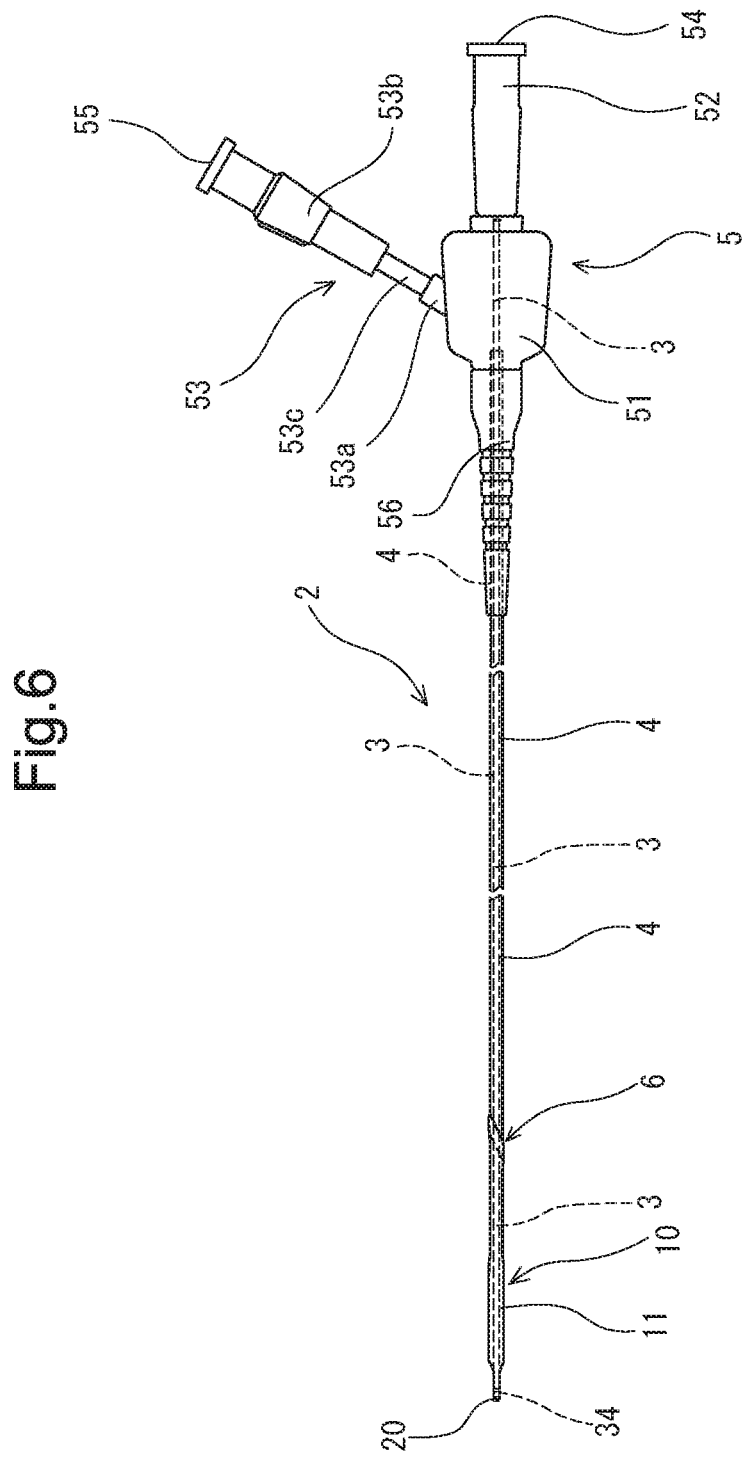
FIG. 6 is a partly abbreviated outside view of a vascular occlusion balloon catheter for use in the balloon catheter assembly shown in FIG. 1

As shown in FIG. 3, in the balloon catheter 2 of this embodiment, the inner tube 3 has an inner layer 32, an outer layer 33, a rigidity imparting body 35, and an imaging marker 34. As shown in FIGS. 4 and 5, the rigidity imparting body 35 is wound around the inner layer 32 and covered with the outer layer 33. Thus, the rigidity imparting body 35 is positioned inside a wall of the inner tube 3 and at a lower portion of the outer layer 33. Resin forming the outer layer 33 is present between filamentous forming the rigidity imparting body 35 embedded in the lower portion of the outer layer 33.

The inner tube 3 is a tubular body open at its distal end and having the main lumen 21. The main lumen 21 is used to insert a guide wire therein to and inject a liquid medicine therein to. In the balloon catheter 2 of this embodiment, the main lumen 21 of the inner tube 3 communicates with a first open portion 54 formed on the branch hub 5.

It is favorable to set the outer diameter of the inner tube 3 to 0.50 to 1.6 mm and more favorable to set the outer diameter thereof to 0.60 to 1.0 mm. It is favorable to set the inner diameter of the inner tube 3 to 0.3 to 1.3 mm and more favorable to set the inner diameter thereof to 0.4 to 0.8 mm.

The inner tube 3 is inserted into the outer tube 4 with a distal end portion of the inner tube projecting beyond the outer tube 4. The second lumen (balloon expanding lumen) 22 is formed between an outer surface of the inner tube 3 and an inner surface of the outer tube 4 and has a sufficiently large volume.

A ring-shaped imaging marker 34 is fixed to a small-diameter distal end portion 37 of the inner tube 3. It is preferable to form the imaging marker of a radiopaque material (for example, gold, platinum, tungsten or alloys of these metals or a silver-palladium alloy, a platinum-iridium alloy, and the like). Thereby it is possible to check the distal end portion of the balloon catheter 2 under X-ray fluoroscopy.

Figure 11:
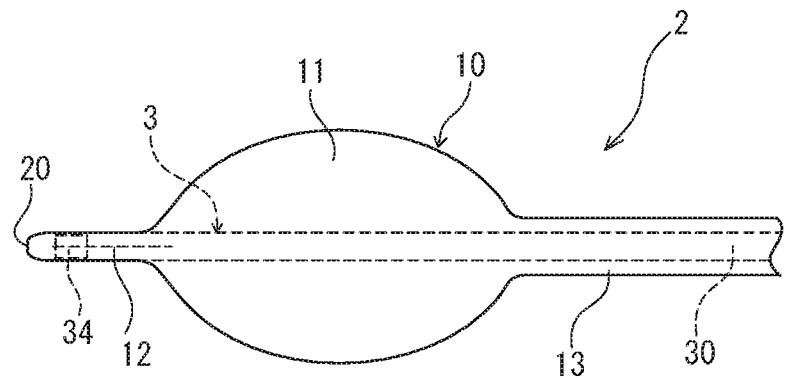
FIG. 11 is an enlarged outside view of the front side part of the balloon catheter shown in FIG. 6 when the balloon thereof is expanded.

The balloon 10 to be used in this embodiment is elastically deformable. In this embodiment, the balloon 10 has a bulged part 11 formed by plastic deformation, a distal side tubular part 12 which is formed at a distal side of the bulged part 11 and smaller than the bulged part 11 in its diameter and thicker than the bulged part 11, and a proximal side tubular part 13 which is formed at a proximal side of the bulged part 11 and smaller than the bulged part 11 in its diameter and thicker than the bulged part 11. The bulged part 11 can be extended owing to elastic deformation caused by an internal pressure applied thereto and is shaped into a diameter-decreased form having wrinkles extending axially. As shown in FIG. 11, the balloon 10 is expandable and clings around the outer periphery of the inner tube 3.

The bulged part 11 of the balloon 10 is expanded by a liquid injected therein to and is capable of closely contacting an inner wall of a blood vessel. More specifically, the bulged part 11 is elastically restored to an originally shaped form from a configured diameter-decreased form by the liquid injected therein to and thereafter extendable (expandable). Thereby the bulged part 11 securely closely contacts the inner wall of the blood vessel without damaging the inner wall thereof. In this embodiment, the bulged part 11 is formed by stretching a material therefore at temperatures not less than its glass transition point and less than its softening point. The bulged part 11 expands without resistance until its plastic deformation shaped form (until original shaped form). Thereafter, the bulged part 11 is elastically expanded (extended) according to the degree of a pressure of the balloon expanding liquid injected therein to. Thereafter, with a decrease in the degree of the pressure of the liquid injected therein to, the bulged part 11 is elastically restored to a form before the bulged part is expanded.

The bulged part 11 is thinner than that of the distal side tubular part 12 and that of the proximal side tubular part 13. The distal side tubular part 12 and the proximal side tubular part 13 are not substantially stretched in the radial direction thereof. An end portion 17 of the distal side tubular part 12 of the bulged part 11 and an end portion 16 of the proximal side tubular part 13 of the bulged part 11 are formed as thickness change portions which become gradually thinner toward the bulged part 11.

The distal side tubular part 12 is a short tubular portion extending in almost an equal outer diameter and having a larger thickness than the bulged part 11. The proximal side tubular part 13 extends in almost an equal outer diameter and is longer than the distal side tubular part 12 in the axial direction thereof. The proximal side tubular part 13 is thicker than the bulged part 11. The distal side tubular part 12 has a smaller outer diameter than the proximal side tubular part 13 and is fixed to the distal end portion of the inner tube 3. It is preferable to fix the distal side tubular part 12 to the inner tube 3 by means of heat sealing.

The proximal side tubular part 13 is not substantially expanded by the liquid injected into the balloon 10. The proximal side tubular part 13 forms a part of the balloon expanding lumen 22 between an inner surface thereof and an inner surface of the inner tube 3. By providing the rear side of the balloon 10 with the proximal side tubular part 13 which extends at a predetermined length in the axial direction thereof, the rear side of the balloon 10 is deformable because the rear side thereof is more flexible than the outer layer 4. Thereby it is possible to accomplish low profiling, i.e., it is possible to decrease the diameter of the rear side of the balloon 10 in inserting the balloon catheter 2 into a living body. That is, the balloon catheter 2 can be easily inserted into a lumen (for example, blood vessel) having a small diameter.

As materials to be used to form the balloon 10, elastic thermoplastic synthetic resins are used. Especially, synthetic resin such as urethane-based elastomer (for example, polyurethane elastomer), olefin-based elastomer (for example, polyethylene elastomer, polypropylene elastomer), polyester (for example, polyethylene terephthalate), soft polyvinyl chloride, amide-based elastomer (for example, polyamide elastomer), fluororesin elastomer and ethylene-vinyl acetate copolymer are favorable. More specifically, thermoplastic polyurethane elastomer (for example, aromatic thermoplastic polyurethane elastomer, and aliphatic thermoplastic polyurethane elastomer) is more favorable. Examples of the thermoplastic polyurethane elastomer include aromatic and aliphatic thermoplastic elastomer polyurethanes.

As materials to be used to form the balloon 10, materials having a glass transition point not more than 0 degrees C. are favorable and those having the glass transition point not more than −10 degrees C. are more favorable. Materials having a softening point (Vicat softening point) not less than 70 degrees C. are also favorable and those having the softening point in a range from 80 degrees C. to 130 degrees C. are more favorable. The balloon 10 has higher flexibility and pliability than the outer tube 4. It is preferable that the balloon 10 has higher flexibility and pliability than the inner tube 3 and the outer tube 4.

It is preferable that the proximal side tubular part 13 is set longer than the distal side tubular part 12 in the axial direction thereof and extended toward the distal end portion of the balloon 10. By setting the length of the proximal side tubular part 13 in the above-described manner, the balloon 10 is allowed to have a long length and thus it is possible to form a long low profiling portion at a portion of the distal side of the balloon catheter.

Figure 7:
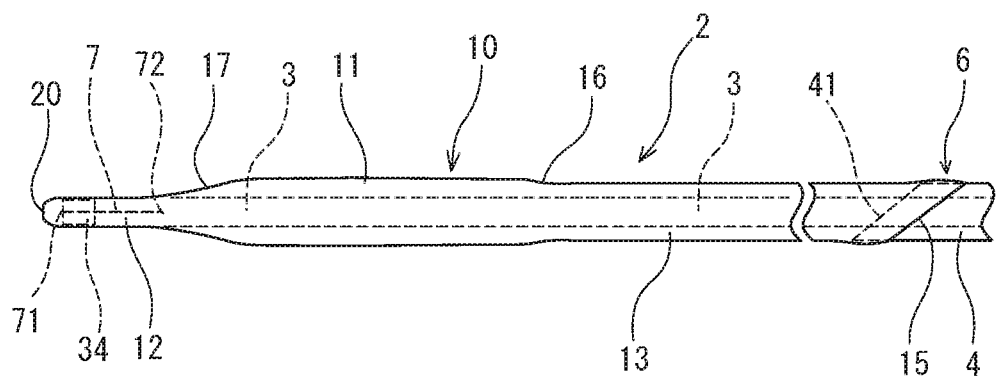
FIG. 7 is an enlarged outside view of a front side part of the balloon catheter shown in FIG. 6.
Figure 12:
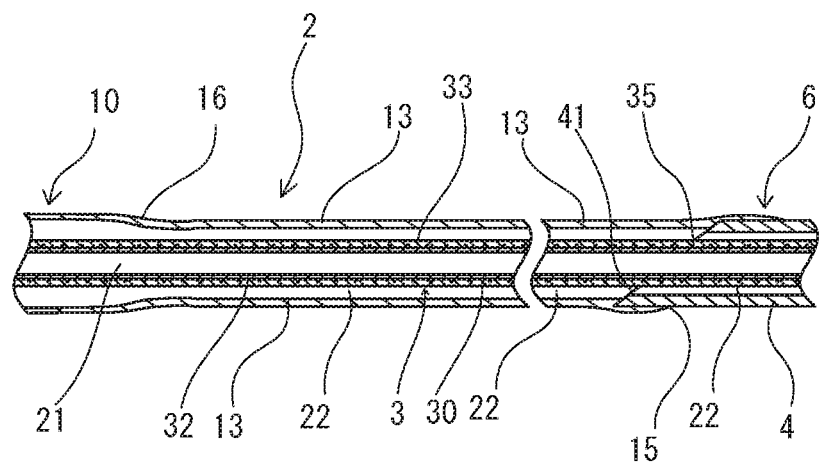
FIG. 12 is an explanatory view for explaining a fixing portion where a distal end portion of an outer tube is fixed to a distal end portion of the balloon of the vascular occlusion balloon catheter shown in FIG. 6.

As shown in FIGS. 7 and 12, the proximal side tubular part 13 of the balloon 10 of this embodiment has a tubular portion extended at a predetermined length toward the distal end portion of the balloon 10. The proximal side tubular part 13 has an inclined proximal end surface 15 oblique to the central axis of the tubular portion. As described later, the proximal side tubular part 13 of the balloon 10 and a distal end portion of the outer tube 4 incline with respect to the central axis of the outer tube 4 and are fixed to a belt-shaped inclined annular fixing portion 6 formed air tightly.

In the balloon 10, the outer diameter (outer diameter when the bulged part is restored to shaped form) of the bulged part 11 is set to favorably 0.90 to 2.10 mm and more favorably 0.93 to 1.00 mm. The outer diameter (expandable outer diameter) of the bulged part 11 is set to favorably 3.0 to 15.0 mm and more favorably 4.0 to 8.0 mm when the bulged part expands. The length of the bulged part 11 is set to favorably 3.5 to 14.5 mm and more favorably 4.0 to 5.5 mm. The radial stretch degree of the bulged part 11 is set to preferably 300 to 900%. The axial stretch degree of the bulged part 11 is set to preferably 200 to 350%.

The outer diameter of the distal side tubular part 12 is set to favorably 0.70 to 1.85 mm and more favorably 0.80 to 0.90 mm. The axial length of the distal side tubular part 12 is set to favorably 2.0 to 7.0 mm and more favorably 3.0 to 6.0 mm. The outer diameter of the proximal side tubular part 13 is set to favorably 0.90 to 2.10 mm and more favorably 0.93 to 1.00 mm. The axial length of the proximal side tubular part 13 is set to favorably 10 to 60 mm and more favorably 15 to 30 mm.

As described above, the bulged part 11 of the balloon 10 is thinner than the distal side tubular part 12 and the proximal side tubular part 13. It is favorable to set the thickness of the bulged part 11 smaller than that of the proximal side tubular part 13 and that of the distal side tubular part 12 by 0.03 to 0.18 mm and more favorable to set the thickness thereof smaller than that of the proximal side tubular part and that the distal side tubular part by 0.04 to 0.11 mm. It is favorable to set the thickness of the proximal side tubular part 13 and that of the distal side tubular part 12 to 0.07 to 0.20 mm and more favorable to set the thickness thereof to 0.08 to 0.15 mm.

It is preferable that the balloon 10 is fixed to the shaft part with the balloon 10 being axially stretched. Therefore, as shown in FIGS. 2 and 7, the balloon 10 is a little stretched axially. Thus, there is a further decrease in the diameter of the bulged part 11 shaped into a diameter-decreased form.

The balloon catheter 2 has the air discharge passage 7 whose distal end opening 71 is positioned distally from the balloon 10 and whose proximal end 72 communicates with the inside of the distal end portion of the balloon 10. As shown in FIG. 3, in the balloon catheter 2 of this embodiment, the distal end opening 71 is positioned inside a portion disposed proximally from the distal end of the balloon catheter 2. The air discharge passage 7 communicates with the main lumen 21 at the distal end opening 71. As described above, the distal end opening 71 of the air discharge passage 7 is positioned inside the portion disposed proximally from the distal end of the balloon catheter 2. The distal end opening 71 is not exposed to the outside. As shown in FIG. 3, in the balloon catheter 2 of this embodiment, the distal end opening 71 of the air discharge passage 7 is positioned at the distal end of the inner tube 3.

The balloon catheter 2 of this embodiment has a distal end portion 20 as shown in FIG. 3. The distal end portion 20 of the balloon catheter of this embodiment decreases toward its distal end in its outer and inner diameters. An inner surface of the distal end portion of the balloon catheter 2 is formed as an annular bulged portion bulged toward a center portion of the main lumen 21. Therefore, the distal end portion 20 has a thickness to some extent as whole and thus sufficiently high configuration retainability. On the other hand, the distal end portion 20 is thin in the vicinity of the distal end opening 71 of the air discharge passage 7. Therefore, the distal end portion 20 displays a high degree of flexibility and is thus obstructive to the discharge of air from the distal end opening 71. As shown in FIG. 3, an inner surface of the distal end portion 20 is positioned forward from the distal end opening 71 of the air discharge passage 7. Therefore, air and the balloon expanding liquid which have flowed out from the distal end opening 71 of the air discharge passage 7 are brought into contact with the inner surface of the distal end portion 20. As shown in FIG. 3, in the balloon catheter 2 of this embodiment, the inner surface of the distal end portion 20 is proximate to the distal end opening 71 of the air discharge passage 7. Thus, the inner surface of the distal end portion 20 constitutes an obstacle to the flow-out of the air and the balloon expanding liquid.

As shown in FIG. 3, in the balloon catheter 2 of this embodiment, an air discharge guide groove 73 which is continuous with the distal end opening 71 of the air discharge passage 7 and extended to the distal end of the balloon catheter 2 is formed on the inner surface of the distal end portion 20. A distal end 73a of the air discharge guide groove 73 is positioned at the distal end of the balloon catheter 2. The air discharge guide groove 73 allows air to be preferably discharged and prevents the air from being stored inside the distal end portion of the balloon catheter 2 when the inner surface of the distal end portion 20 contacts an outer surface of the shaft part 91 of the mandrel 9. As shown in FIG. 3, in the balloon catheter 2 of this embodiment, a distal end 20 of a distal side tubular portion 12a of the balloon 10 is projected from the distal end of the inner tube 3. By shaping the distal end 20 into a necessary configuration, the distal end portion 20 of the balloon catheter 2 is formed.

The air discharge passage 7 has the area of 200 $\mu m^2$ to 450 $\mu m^2$ in the cross section thereof orthogonal to the axial direction of the balloon catheter 2 and has a length of 1.0 to 3.0 mm.

It is preferable to set the area of the balloon catheter 2 in the cross section thereof orthogonal to the axial direction thereof to 250 $\mu m^2$ to 350 $\mu m^2$ and the length of the air discharge passage to 1.0 to 2.0 mm.

Figure 10:
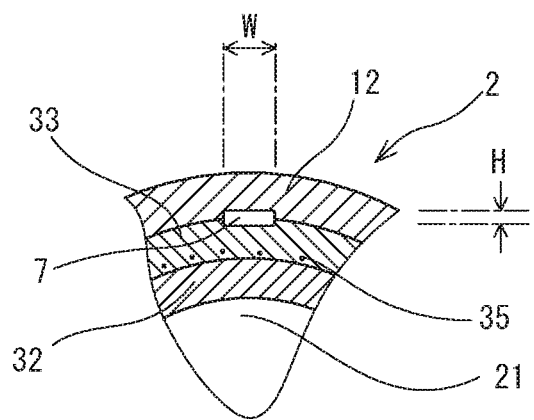
FIG. 10 is an explanatory view for explaining the form of an air discharge passage of the vascular occlusion balloon catheter of the embodiment of the present invention.

It is preferable that the air discharge passage 7 has a form whose configuration in a cross section orthogonal to the axial direction of the balloon catheter 2 is elongated in a circumferential direction of the balloon catheter 2. With reference to FIG. 10, it is favorable that in the cross section of the air discharge passage orthogonal to the axial direction of the balloon catheter, a length W of the air discharge passage 7 in the circumferential direction of the balloon catheter 2 is set to 1 to 1.5 times as large as a width H of the air discharge passage. It is more preferable to set the length W two to four times as large as the width H. Although it is preferable that the cross section of the air discharge passage 7 orthogonal to the axial direction of the balloon catheter 2 has a rectangular configuration elongated in the circumferential direction of the balloon catheter 2 as shown in FIG. 10, the air discharge passage 7 may have an elliptic sectional configuration having a major axis in the circumferential direction of the balloon catheter 2 and a minor axis in the radial direction thereof. The sectional configuration of the air discharge passage 7 may be a perfect circle, may be extended in a predetermined length and in the same height in the circumferential direction of the balloon catheter 2 or may be bulged at both sides of the air discharge passage 7 like a gourd. The air discharge passage 7 may be so constructed as to allow the discharge of air and make it difficult for the balloon expanding liquid to enter therein to.

As shown in FIG. 10, the entire air discharge passage 7 has the form in which the configuration of the air discharge passage 7 in the cross section thereof orthogonal to the axial direction of the balloon catheter 2 is elongated in the circumferential direction of the balloon catheter 2, as described above. By elongating the cross section of the air discharge passage 7 in the central axis direction of the balloon catheter 2, it is possible to decrease the width (length of minor axis) of an air discharge port and thereby reduce an increase of the outer diameter of the balloon catheter as much as possible. Because the air discharge port 7 is elongated in the circumferential direction of the balloon catheter 2, the air discharge port displays a sufficiently high discharge function.

As shown in FIG. 3, in the balloon catheter 2 of this embodiment, the air discharge passage 7 is formed between the inner surface of the balloon 10 and the inner tube 3. More specifically, the air discharge passage 7 is positioned between the outer surface of the imaging marker 34 and a distal end thin portion 12a of the balloon 10 at the distal end portion thereof and positioned between the outer surface of the inner tube 3 and the distal end portion of the balloon 10 at the proximal end portion thereof.

Thus, in the balloon catheter 2 of this embodiment, the shaft part has the ring-shaped imaging marker 34 provided at the distal end portion of the inner tube 3 and a marker covering portion (distal side thin portion 12a) covering the ring-shaped imaging marker 34. A part of the air discharge passage 7 is extended between the ring-shaped imaging marker and the marker covering portion (distal side thin portion 12a).

It is possible to use the bulged part 11, of the balloon 10, which is shaped by plastic deformation and can be expanded by elastic deformation. In the balloon 10 of this type, the bulged part 11 can be extended (expanded) by the elastic deformation by applying an internal pressure to the balloon 10 and is restored to a configuration before it is elastically deformed by releasing the applied internal pressure. The distal side tubular part 12 and the proximal side tubular part 13 are smaller than the bulged part 11 in the diameters thereof and thicker than the bulged part and cannot be substantially expanded.

The bulged part 11 of the balloon 10 is elastically restored to the originally shaped form by the balloon—expanding liquid injected into the balloon and thereafter extendable (expandable). Thereby the bulged part 11 securely closely contacts the inner wall of the blood vessel without damaging the inner wall thereof. The bulged part 11 can be formed by stretching the material used therefore at temperatures not less than its glass transition point and less than its softening point. The bulged part 11 expands without resistance until its plastic deformation shaped form (until originally shaped form). Thereafter, the bulged part 11 is elastically expanded (extended) according to the degree of the pressure of the balloon expanding liquid injected therein to. Thereafter, with a decrease in the degree of the pressure of the liquid injected therein to, the bulged part 11 is elastically restored to the form before the bulged part is expanded.

An air discharge liquid is capable of entering when the air discharge liquid is injected into the balloon 10 having the above-described form to such an extent that the bulged part 11 expands beyond the form shaped by the plastic deformation.

The outer tube 4 is a tubular body into which the inner tube 3 is inserted. A distal end of the outer tube 4 is positioned at a portion rearward or proximal from the distal end of the inner tube 3 at a predetermined length. The distal end of the balloon expanding lumen 22 communicates with the distal end portion of the balloon 10. As described later, the proximal end of the balloon expanding lumen 22 communicates with a second open portion 55 of an injection port 53, provided on a branch hub 5, into which the balloon expanding fluid (for example, balloon expanding liquid, specifically angiographic agent) is injected.

It is favorable to set the outer diameter of the outer tube 4 to 0.85 to 2.03 mm and more favorable to set the outer diameter thereof to 0.87 to 0.95 mm. It is favorable to set the inner diameter of the outer tube 4 to 0.70 to 1.83 mm and more favorable to set the inner diameter thereof to 0.72 to 0.80 mm As materials to be used to form the outer tube 4 and the inner tube 3, materials having hardness and flexibility to some extent are preferable. It is possible to use polyolefin such as polyethylene and polypropylene; polyamide; polyester such as polyethylene terephthalate; fluorine-based polymer such as PTFE and ETFE; PEEK (polyether ether ketone); polyimide; synthetic resin elastomer such as olefinic elastomer (for example, polyethylene elastomer and polypropylene elastomer), polyamide elastomer, styrenic elastomer (for example, a styrene-butadiene-styrene copolymer, a styrene-isoprene-styrene copolymer, a styrene-ethylene butylene-styrene copolymer); polyurethane, urethane-based elastomer, and fluorine-based elastomer; synthetic rubber such as urethane rubber, silicone rubber, and butadiene rubber; and rubbers such as latex rubber and natural rubber.

Figure 8:
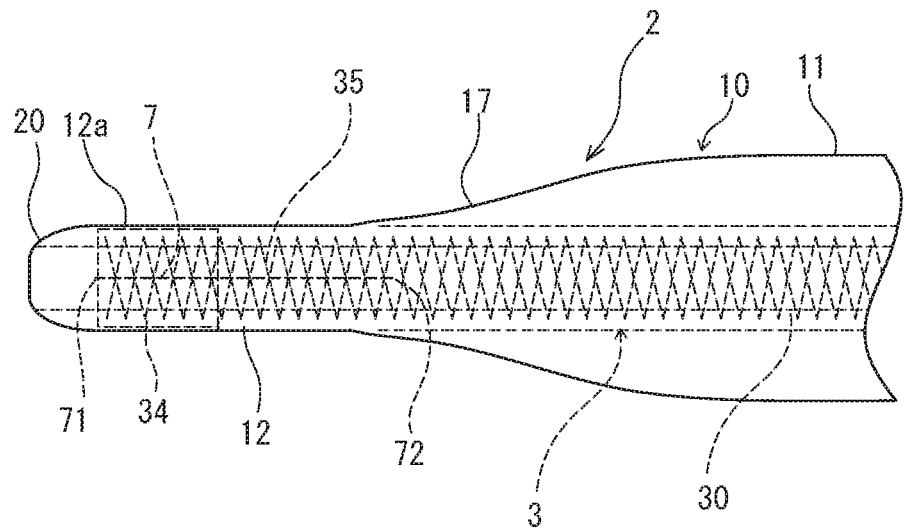
FIG. 8 is an enlarged outside view of a distal end portion of the balloon catheter shown in FIG. 6.
Figure 9:
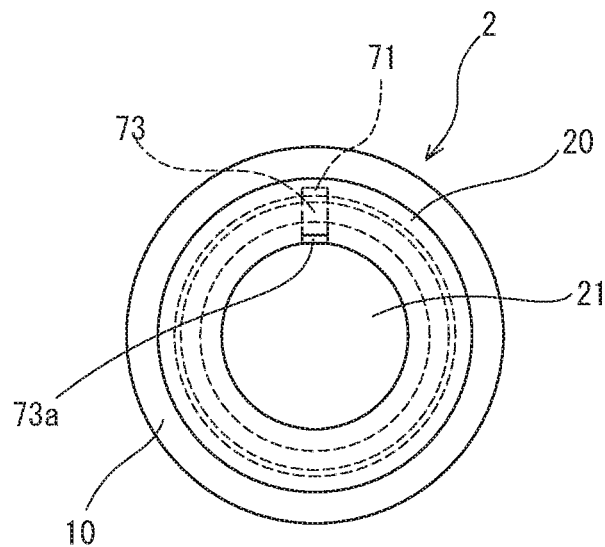
FIG. 9 is an enlarged view as viewed from the front side part of the balloon catheter shown in FIG. 7.

The outer tube 4 and the inner tube 3 may be provided with a rigidity imparting body 35. As a material for the rigidity imparting body 35, a braid formed of a metal wire or a synthetic resin wire is preferable. As shown in FIG. 8, in a case where the rigidity imparting body 35 is mounted on the inner tube 3, it is desirable to mount rigidity imparting body 35 thereon entirely except the distal end portion thereof. More specifically, it is preferable to mount the rigidity imparting body 35 on the inner tube 3 in the range from the position of the imaging marker 34 to the proximal end thereof.

With reference to FIGS. 7 and 12, description is made below on an inclined annular fixing portion (in other words, inclined annular joining portion) for joining the proximal side tubular part 13 of the balloon 10 of the balloon catheter of this embodiment and the distal end portion of the outer tube 4 with each other.

The outer tube 4 has an inclined distal end surface 41 oblique to the central axis of the outer tube 4 disposed at the distal end portion thereof. The balloon 10 has an inclined proximal end surface 15 oblique to the central axis of the proximal side tubular part 13 disposed at the proximal side tubular part 13 thereof. The distal end portion of the outer tube 4 and the proximal side tubular part 13 of the balloon 10 overlap each other at a portion in the axial direction of the balloon catheter.

The balloon catheter 2 has a belt-shaped inclined annular fixing portion 6 provided at a portion where the distal end portion of the outer tube 4 and the proximal side tubular part 13 of the balloon 10 overlap each other. The inclined annular fixing portion 6 inclines with respect to the central axis of the outer tube 4 and is formed air tightly. The inclined annular fixing portion 6 allows a gradual change of the property of the fixing portion for fixing the proximal end portion of the balloon of the balloon catheter and the distal end portion of the outer tube 4 to each other. Thus, it does not occur that a portion where the property of the outer tube 4 changes rapidly is formed in the vicinity of the distal end of the outer tube 4 and in the vicinity of the proximal end of the balloon 10. Because there is no change in the property in the above-described portion where the outer tube 4 and the balloon 10 overlap each other, the outer tube 4 and the balloon 10 hardly kink. Thus, it is possible to favorably perform an operation of inserting the balloon catheter into the blood vessel.

Figure 13:
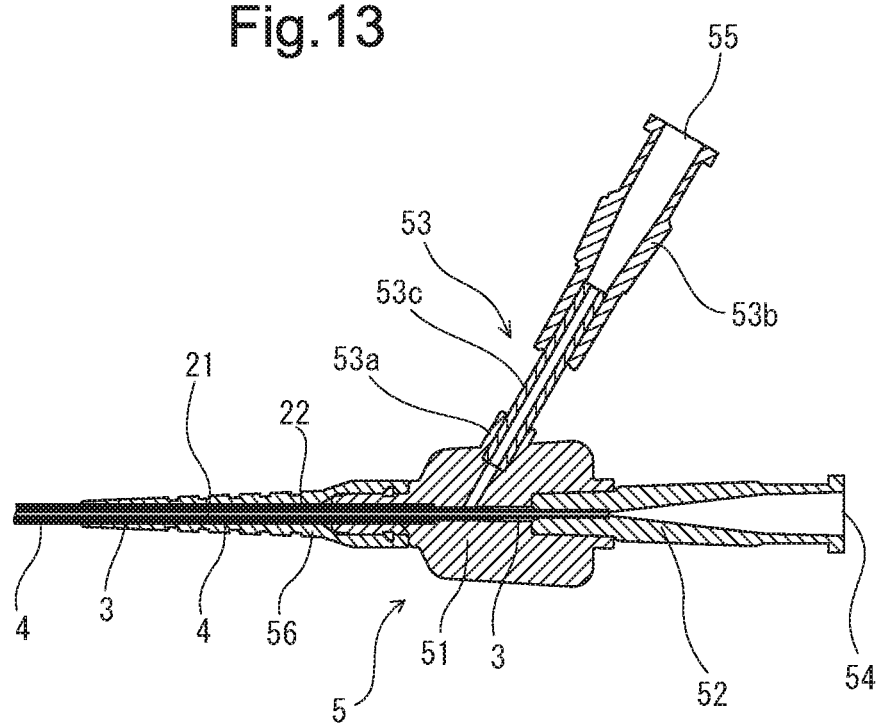
FIG. 13 is an enlarged vertical sectional view of a proximal end portion of the vascular occlusion balloon catheter shown in FIG. 6.

As shown in FIG. 13, the branch hub 5 has an inner tube hub 52 which has a first open portion 54 communicating with the main lumen 21 and is fixed to the proximal end portion of the inner tube 3, an outer tube hub 51 which has a second open portion 55 communicating with the balloon expanding lumen 22 and provided at an end of an injection port 53 and which is fixed to the proximal end portion of the outer tube 4. The outer tube hub 51 and the inner tube hub 52 are fixed to each other. To fix the outer tube hub 51 and the inner tube hub 52 to each other, the distal end of the inner tube 3 is inserted into a proximal end of the outer tube hub 51 mounted on the proximal portion of the outer tube 4.

The branch hub 5 is provided with a bending prevention tube 56 covering the proximal portion of the outer tube 4 and a distal end portion of the branch hub 5. The injection port 53 is formed of a branch port 53a extended from a side wall of the outer tube hub 51, an injection port hub 53b, and a connection tube 53c connecting the branch port 53a and the injection port hub 53b to each other. As materials to be used to form the branch hub and the injection port hub, it is possible to suitably use thermoplastic resin such as polycarbonate, polyamide, polysulfone, polyarylate, and methacrylate-butylene-styrene copolymer. As the connection tube, a synthetic resin tube flexible or soft is used.

The construction of the balloon catheter is not limited to the above-described ones, but the balloon catheter may have a guide wire insertion opening communicating with a guide wire lumen at an intermediate portion (rearward from the inclined annular fixing portion 6) thereof.

As shown in FIGS. 1 through 3, the balloon catheter assembly 1 of the present invention has the sleeve 8 covering the balloon 10 of the balloon catheter 2 and restraining the balloon 10 from expanding. The sleeve 8 is removable from the distal end of the balloon catheter 2.

As the sleeve 8, a tubular member is used. A transparent tubular member allowing the balloon to be visually recognizable is suitably used. It is preferable to use a cylindrical member having a length and an inner diameter to such an extent as to cover the entire bulged part of the balloon 10 for the sleeve 8. The sleeve 8 may be so dimensioned and configured as to cover the entire balloon 10. As shown in FIG. 3, it is preferable that the sleeve 8 can be mounted on the balloon when the balloon is not in an expanded state but in a state in which the balloon is extended a little in its axial direction and is positioned on the balloon so long as the sleeve is not operated. It is also preferable that the sleeve 8 is flexible to some extent.

As shown in FIGS. 1 through 3, the balloon catheter assembly 1 of the present invention has the mandrel 9 which enters the balloon catheter 2 from the distal end opening thereof and the distal end of which reaches into the main lumen 21 after the mandrel 9 passes the distal end opening 71 of the air discharge passage 7. The mandrel 9 can be removed from the balloon catheter 2 from its distal end.

The mandrel 9 of this embodiment has a shaft part 91 and a gripping part 92 fixed to the proximal end of the shaft part 91. As the material for the shaft part 91, a linear body rigid to some extent is preferable. For example, a metal wire can be preferably used.

The shaft part 91 used in this embodiment has an outer diameter a little smaller than the inner diameter of the distal end portion 20 of the balloon catheter 2 and the inner diameter of the inner tube (inner diameter of the main lumen). The shaft part 91 used in this embodiment has a length so dimensioned that its distal end is capable of reaching into at least the inner tube (into the main lumen). To prevent the shaft part 91 from kinking at the distal end of the sleeve 8 during a priming operation, it is preferable for the shaft part 91 to have a length so dimensioned that its distal end is disposed proximally from the distal end of the sleeve 8 and more preferable for the shaft part 91 to have a length so dimensioned that its distal end is disposed proximally from the proximal end of the bulged part 11. The shaft part 91 may be so formed that its distal end has a reduced diameter. Thereby the shaft part 91 can be easily inserted into the distal end opening of the balloon catheter 2.

In the balloon catheter assembly 1 of this embodiment, as shown in FIGS. 1 through 3, the priming operation of replacing air inside the balloon expanding lumen 22 with a liquid is performed with the sleeve 8 and the mandrel 9 being mounted on the balloon catheter 2.

In the priming operation, a syringe in which a priming liquid has been filled is mounted on the open portion 55 of the injection port 53 provided on the outer tube hub 51 of the branch hub 5. The distal side of the balloon catheter assembly 1 (more specifically, part in the range from the distal end of the assembly to a position rearward from the proximal end of the sleeve 8) is immersed in the liquid.

Thereafter the syringe is operated to inject the priming liquid to the balloon expanding lumen 22. Thereby air inside the balloon expanding lumen 22 and the balloon 10 is pressed by the priming liquid injected into the balloon expanding lumen 22 and consequently transferred inside the balloon. The air inside the balloon is flowed out from the distal end opening of the air discharge passage 7 by continuous injection of the priming liquid into the balloon expanding lumen 22. The air flowed out from the distal end opening of the air discharge passage 7 passes through the air discharge guide groove 73 or the gap between the shaft 91 of the mandrel 9 and the distal end portion 20 of the balloon catheter and is discharged from the distal end of the balloon catheter 2.

The balloon 10 is covered with the sleeve 8 and thus the balloon is restrained from expanding. Therefore, a small amount of the priming liquid flows into the balloon 10. Further, because the mandrel 9 is mounted on the balloon catheter assembly, the distal end portion of the balloon catheter 2 is restrained from deforming. Thereby the priming operation can be easily accomplished. Furthermore, the mandrel 9 mounted on the balloon catheter assembly restrains the air which has flowed out from the distal end opening 71 of the air discharge passage 7 open inside the balloon catheter 2 from flowing into the main lumen 21. Thereby the air can be satisfactorily transferred to the distal end of the balloon catheter 2.

Figure 14:
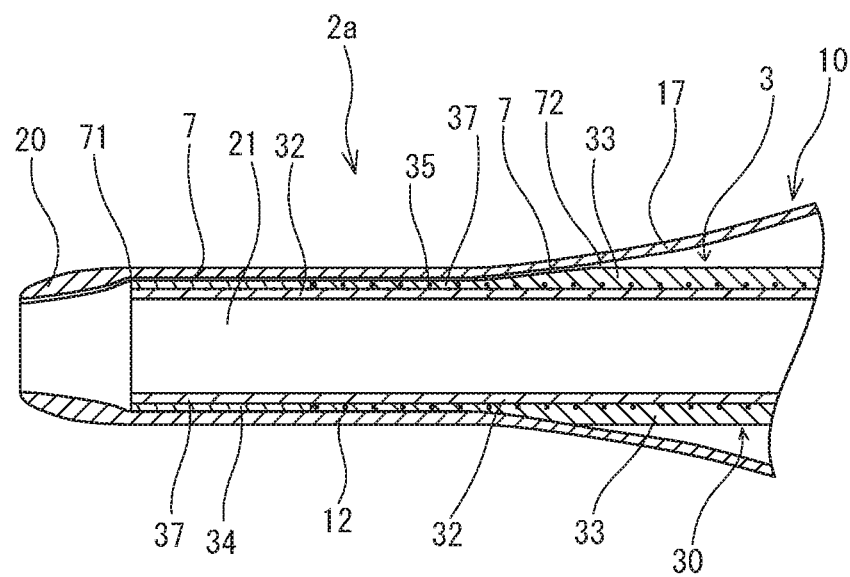
FIG. 14 is an explanatory view for explaining the form of an air discharge passage of a vascular occlusion balloon catheter of another embodiment of the present invention.

In all of the above-described embodiments, the balloon catheter may have the form of a distal end portion of a balloon catheter 2a shown in FIG. 14.

In the balloon catheter 2a of the embodiment shown in FIG. 14, the inner tube body 30 has the small-diameter distal end portion 37 to which the ring-shaped imaging marker 34 is fixed. The distal end opening 71 of the air discharge passage 7 is positioned at the distal end of the imaging marker 34 and the distal end of the inner tube 3.

It is preferable to set the outer diameter of the ring-shaped imaging marker 34 equally to that of the inner tube body 30. The length of the small-diameter distal end portion 37 of the inner tube body 30 is set to favorably 1.0 to 4.0 mm and more favorably 1.0 to 3.0 mm. The outer diameter of the small-diameter distal end portion 37 is set smaller favorably by 0.01 to 0.3 mm and more favorably by 0.02 to 0.2 mm than that of the inner tube except for the small diameter portion thereof.

As shown in FIG. 14, in the balloon catheter 2a of this embodiment, the small-diameter portion 37 is formed of a miss portion of the outer surface layer 33 of the inner tube body 30. More specifically, the small-diameter portion 37 is formed by partially removing the outer surface layer of the outer layer 33. The outer surface layer is partially removed by scraping the outer surface layer or dissolving it with a solvent capable of dissolving it. In this embodiment, the rigidity imparting body 35 is formed extended to the distal end portion of the small-diameter portion 37 and not provided at the portion where the imaging marker 34 is disposed.

Figure 15:
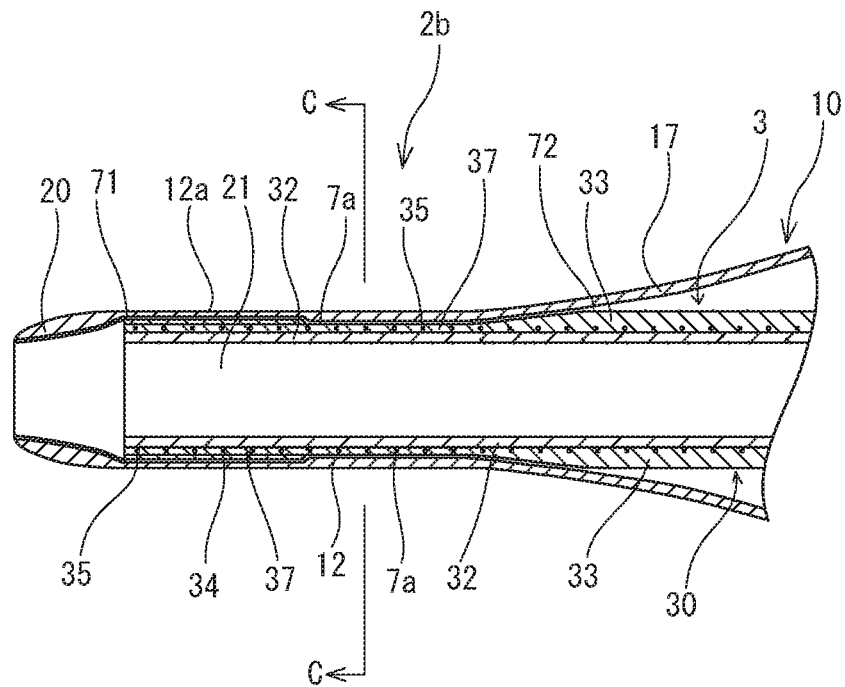
FIG. 15 is an explanatory view for explaining the form of an air discharge passage of a vascular occlusion balloon catheter of still another embodiment of the present invention.
Figure 16:
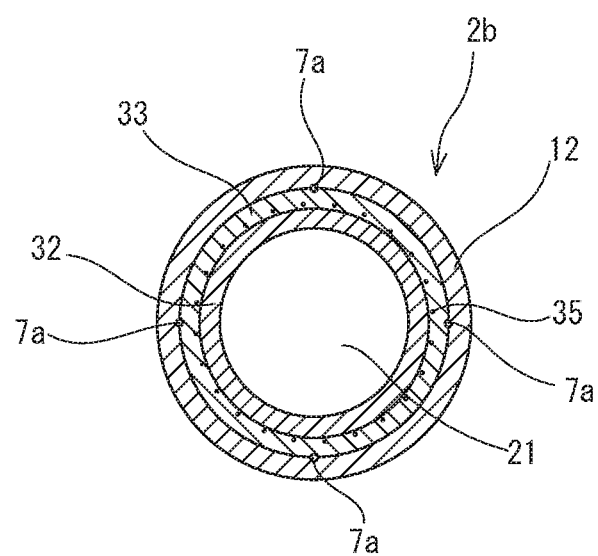
FIG. 16 is a sectional view taken along a line C-C of FIG. 15.

In all of the above-described embodiments, the balloon catheter may have the form of a distal end portion of a balloon catheter 2b shown in FIGS. 15 and 16.

As shown in FIGS. 15 and 16, the balloon catheter 2b of this embodiment has a plurality of air discharge passages 7a. The distal end opening 71 of each air discharge passage 7a is located at a position distal from the balloon of the balloon catheter and inside the balloon catheter. The other end 72 of each air discharge passage 7a communicates with the distal end portion of the inner space of the balloon 10. More specifically, as shown in FIGS. 15 and 16, the air discharge passage 7a of this embodiment has the distal end opening 71 which is open inside the balloon catheter 2b and at the distal end of the inner tube 3 and is extended toward the proximal end of the balloon catheter 2b in its axial direction. The other end 72 of the air discharge passage 7a communicates with the distal end of the space inside the balloon 10

In the balloon catheter 2b of this embodiment, the distal end portion 20 is formed at the distal end of the inner tube 3. The outer surface of the imaging marker 34 is covered with the distal side thin portion 12a of the balloon 10. Thus, the outer surface of the imaging marker 34 is not exposed to the outside.

As shown in FIGS. 15 and 16, in the balloon catheter 2b of this embodiment, the air discharge passage 7a is formed between the inner surface of the balloon 10 and the inner tube 3. More specifically, the distal end portion of the air discharge passage 7a is positioned between the outer surface of the imaging marker 34 and the distal side thin portion 12a of the balloon 10. The proximal end portion of the air discharge passage 7a is positioned between the outer surface of the inner tube 3 and the distal end portion of the balloon 10.

Thus, in the balloon catheter 2b of this embodiment, the shaft part has the ring-shaped imaging marker 34 provided at the distal end portion of the inner tube 3 and the marker covering portion (distal side thin portion 12a) covering the ring-shaped imaging marker 34. A part of the air discharge passage 7a is extended between the ring-shaped imaging marker 34 and the marker covering portion (distal side thin portion 12a).

The air discharge passage 7a of this embodiment has one end (distal end opening) 71 which is open at the distal end surface of the balloon catheter 2b and is extended toward the proximal end of the balloon catheter 2b in its axial direction. The other end 72 of the air discharge passage 7a communicates with the distal end of the inner space disposed inside the balloon 10.

As shown in FIGS. 15 and 16, the balloon catheter 2b has a plurality of the air discharge passages 7a. The air discharge passages 7a are extended almost parallel with the central axis of the inner tube 3.

It is favorable to set the number of the air discharge passages 7a to two to four and more favorable to set the number thereof to two to three. The total of the areas of the cross sections of the air discharge passages 7 orthogonal to the axial direction of the balloon catheter 2b is set to 200 $\mu m^2$ to 450 $\mu m^2$. It is favorable to set the total of the areas of the cross sections of the air discharge passages 7 orthogonal to the axial direction of the balloon catheter 2b to 250 $\mu m^2$ to 350 $\mu m^2$.

It is favorable to set the area of the cross section of each of the air discharge passages 7a orthogonal to the axial direction of the balloon catheter 2b to 50 to 200 $\mu m^2$. It is favorable to set the length of each of the air discharge passages 7a to 1.0 to 2.0 mm.

As shown in FIG. 16, although it is preferable to shape the section of the air discharge passage 7a of this embodiment orthogonal to the axial direction of the balloon catheter into almost a perfect circle, the sectional configuration of the air discharge passage 7a may be elongated in the axial direction of the balloon catheter or elongated to some extent in the axial direction of the balloon catheter.

The vascular occlusion balloon catheter of the present invention has the following form:

(1) A vascular occlusion balloon catheter comprising a vascular occlusion balloon and a shaft part having a main lumen and a balloon expanding lumen, wherein said vascular occlusion balloon catheter has an air discharge passage, said air discharge passage has a distal end opening located at a position distal from said vascular occlusion balloon and a proximal end communicating with an inner portion of said vascular occlusion balloon, said distal end opening of said air discharge passage is positioned inside a portion disposed proximally from a distal end of said vascular occlusion balloon catheter, said air discharge passage communicates with said main lumen at said distal end opening of said air discharge passage, and an area of a cross section of said air discharge passage orthogonal to an axial direction of said vascular occlusion balloon catheter is set to 200 $\mu m^2$ to 450 $\mu m^2$, and a length of said air discharge passage is set to 1.0 to 3.0 mm.

The above-described embodiment may have the following forms:

(2) A vascular occlusion balloon catheter according to the above (1), further comprising a sleeve which covers said balloon and restrains said balloon from expanding, wherein said sleeve is removal from said distal end of said balloon catheter.

(3) A vascular occlusion balloon catheter according to the above (1) or (2), further comprising a mandrel entering said balloon catheter from said distal end opening thereof, passing a position of said distal end opening of said air discharge passage, and entering into said main lumen, wherein said mandrel is removal from said distal end of said balloon catheter.

(4) A vascular occlusion balloon catheter according to any one of the above (1) through (3), further comprising an air discharge guide groove which is continuous with said distal end opening of said air discharge passage and extended to said distal end of said balloon catheter is formed on an inner surface of a distal end portion of said balloon catheter.

(5) A vascular occlusion balloon catheter according to any one of the above (1) through (4), wherein an area of said balloon catheter in a cross section thereof orthogonal to an axial direction thereof is set to 250 $\mu m^2$ to 350 $\mu m^2$.

(6) A vascular occlusion balloon catheter according to any one of the above (1) through (5), wherein a length of said air discharge passage is set to 1.0 to 2.0 mm.

(7) A vascular occlusion balloon catheter according to any one of the above (1) through (6), wherein said air discharge passage orthogonal to said axial direction of said balloon catheter is elongated in a circumferential direction of said balloon catheter.

(8) A vascular occlusion balloon catheter according to any one of the above (1) through (7), wherein said distal end portion of said balloon catheter decreases toward said distal end thereof in outer and inner diameters thereof; and said inner surface of said distal end portion of said balloon catheter is formed as an annular bulged part and is positioned forward from said distal end opening of said air discharge passage.

(9) A vascular occlusion balloon catheter according to any one of the above (1) through (8), wherein said shaft part has an inner tube and an outer tube coaxial with said inner tube and having a distal end thereof at a position rearward at a predetermined length from a distal end of said inner tube; said balloon has a bulged part, a distal side tubular part extended from a distal end of said bulged part, and a proximal side tubular part extended from a proximal end of said bulged part; and said distal side tubular part is fixed to said inner tube and said proximal side tubular part is fixed to said outer tube.

(10) A vascular occlusion balloon catheter according to the above (9), wherein a distal end of said distal side tubular portion of said balloon is projected from a distal end of said inner tube and forms said distal end portion of said balloon catheter; and said distal end opening of said air discharge passage is positioned at said distal end of said inner tube.

(11) A vascular occlusion balloon catheter according to the above (9) or (10), wherein said shaft part has a ring-shaped imaging marker provided at a distal end portion thereof; said distal side tubular part of said balloon has a marker covering portion covering said ring-shaped imaging marker; and a part of said air discharge passage is extended between said ring-shaped imaging marker and said marker covering portion.

(12) A vascular occlusion balloon catheter according to any one of the above (1) 1 through (11), wherein said balloon has a bulged part which can be elastically deformed by a liquid injected therein to and plastically deformed after said bulged part is elastically deformed.

What is claimed is:

1. A vascular occlusion balloon catheter comprising a vascular occlusion balloon and a shaft part having a main lumen and a balloon expanding lumen, wherein said vascular occlusion balloon has an inner portion, said main lumen is open at a distal end of said the vascular occlusion balloon catheter, said balloon expanding lumen is located outside said main lumen, and a distal end of the balloon expanding lumen communicates with a proximal end of said inner portion of the vascular occlusion balloon, said vascular occlusion balloon catheter has an air discharge passage, said air discharge passage has a distal end opening located on a distal end side of said vascular occlusion balloon catheter with respect to a distal end of said inner portion of said vascular occlusion balloon and a proximal end communicating with said distal end of said inner portion of said vascular occlusion balloon, said distal end opening of said air discharge passage is located on a distal inside portion of said vascular occlusion balloon catheter, said air discharge passage communicates with said main lumen at said distal end opening of said air discharge passage, said air discharge passage has a cross-sectional area of 200 μm² to 450 μm² in a cross section orthogonal to an axial direction between said distal end opening and said proximal end of the air discharge passage, and a length of the air discharge passage between said distal end opening and said proximal end is 1.0 to 3.0 mm.

2. A vascular occlusion balloon catheter according to claim 1, further comprising a sleeve which covers said vascular occlusion balloon and restrains said vascular occlusion balloon from expanding and is removable from said distal end of said balloon catheter.

3. A vascular occlusion balloon catheter according to claim 1, further comprising a mandrel entering said balloon catheter from a distal end opening of said balloon catheter, passing a position of said distal end opening of said air discharge passage, and entering into said main lumen,
wherein said mandrel is removable from said distal end of said balloon catheter.

4. A vascular occlusion balloon catheter according to claim 1, further comprising an air discharge guide groove which is extended to said distal end of said balloon catheter and is formed on an inner surface of a distal end portion of said balloon catheter, and a proximal end of said air discharge guide groove faces said distal end opening of said air discharge passage.

5. A vascular occlusion balloon catheter according to claim 1, wherein said cross-sectional area is 250 μm² to 350 μm².

6. A vascular occlusion balloon catheter according to claim 1, wherein said length is 1.0 to 2.0 mm.

7. A vascular occlusion balloon catheter according to claim 1, wherein said air discharge passage has a form whose configuration in a cross section orthogonal to said axial direction of said vascular occlusion balloon catheter is elongated in a circumferential direction of said vascular occlusion balloon catheter with respect to a radial direction of said vascular occlusion balloon catheter.

8. A vascular occlusion balloon catheter according to claim 1, wherein a distal end portion of said balloon catheter decreases toward said distal end of said balloon catheter in outer and inner diameters thereof; and an inner surface of said distal end portion of said balloon catheter is formed as an annular bulged part and is positioned distal of said distal end opening of said air discharge passage.

9. A vascular occlusion balloon catheter according to claim 1, wherein said shaft part has an inner tube and an outer tube coaxial with said inner tube and having a distal end of the outer tube at a position rearward at a predetermined length from a distal end of said inner tube; said vascular occlusion balloon has a bulged part, a distal side tubular part extended from a distal end of said bulged part, and a proximal side tubular part extended from a proximal end of said bulged part; and said distal side tubular part is fixed to said inner tube and said proximal side tubular part is fixed to said outer tube.

10. A vascular occlusion balloon catheter according to claim 9, wherein a distal end of said distal side tubular portion of said vascular occlusion balloon is projected from a distal end of said inner tube and forms said distal end portion of said balloon catheter; and said distal end opening of said air discharge passage is positioned at said distal end of said inner tube.

11. A vascular occlusion balloon catheter according to claim 9, wherein said shaft part has a ring-shaped imaging marker provided at a distal end portion thereof; said distal side tubular part of said vascular occlusion balloon has a marker covering portion covering said ring-shaped imaging marker; and a part of said air discharge passage is extended between said ring-shaped imaging marker and said marker covering portion.

12. A vascular occlusion balloon catheter according to claim 1, wherein said vascular occlusion balloon has a bulged part which can be elastically deformed by a liquid injected thereinto and plastically deformed after said bulged part is elastically deformed.

13. A vascular occlusion balloon catheter according to claim 1, further comprising an annular bulged part provided to an inner surface of a distal end portion of said vascular occlusion balloon catheter, and said annular bulged part is positioned distal of said distal end opening of said air discharge passage.

14. A vascular occlusion balloon catheter comprising a vascular occlusion balloon and a shaft part having a main lumen and a balloon expanding lumen,
wherein said vascular occlusion balloon has an inner portion, said main lumen is open at a distal end of said the vascular occlusion balloon catheter, said balloon expanding lumen is located outside said main lumen, and a distal end of the balloon expanding lumen communicates with a proximal end of said inner portion of the vascular occlusion balloon, said vascular occlusion balloon catheter has an air discharge passage, said air discharge passage has a distal end opening located on a distal end side of said vascular occlusion balloon catheter with respect to a distal end of said inner portion of said vascular occlusion balloon and a proximal end communicating with said distal end of said inner portion of said vascular occlusion balloon, said distal end opening of said air discharge passage is located on a distal inside portion of said vascular occlusion balloon catheter, said air discharge passage communicates with said main lumen at said distal end opening of said air discharge passage, said vascular occlusion balloon catheter has an annular bulged part provided to an inner surface of a distal end portion of said vascular occlusion balloon catheter and positioned distal of said distal end opening of said air discharge passage, and said vascular occlusion said balloon catheter has an air discharge guide groove formed on said inner surface of said distal end portion of said vascular occlusion balloon catheter and extending to said distal end of said vascular occlusion balloon catheter, and a proximal end of said air discharge guide groove faces said distal end opening of said air discharge passage.

15. A vascular occlusion balloon catheter according to claim 14, wherein said air discharge passage has a cross-sectional area of 200 $\mu m^2$ to 450 $\mu m^2$ in a cross section orthogonal to an axial direction between said distal end opening and said proximal end of the air discharge passage, and a length of the air discharge passage between said distal end opening and said proximal end is 1.0 to 3.0 mm.

16. A vascular occlusion balloon catheter comprising a vascular occlusion balloon and a shaft part having a main lumen and a balloon expanding lumen,
wherein said vascular occlusion balloon has an inner portion,
said main lumen is open at a distal end of said the vascular occlusion balloon catheter,
said balloon expanding lumen is located outside said main lumen, and a distal end of the balloon expanding lumen communicates with a proximal end of said inner portion of the vascular occlusion balloon,
said vascular occlusion balloon catheter has an air discharge passage,
said air discharge passage has a distal end opening located on a distal end side of said vascular occlusion balloon catheter with respect to a distal end of said inner portion of said vascular occlusion balloon and a proximal end communicating with said distal end of said inner portion of said vascular occlusion balloon,
said distal end opening of said air discharge passage is located on a distal inside portion of said vascular occlusion balloon catheter, said air discharge passage communicates with said main lumen at said distal end opening of said air discharge passage,
said vascular occlusion vascular occlusion balloon catheter has a sleeve which covers said vascular occlusion balloon and restrains said vascular occlusion balloon from expanding, and said sleeve is removable from said distal end of said balloon catheter, and
said vascular occlusion vascular occlusion balloon catheter has a mandrel entering said balloon catheter from said distal end opening thereof, passing a position of said distal end opening of said air discharge passage, and entering into said main lumen, and said mandrel is removable from said distal end of said balloon catheter.

17. A vascular occlusion balloon catheter according to claim 16, wherein said air discharge passage has a cross-sectional area of 200 $\mu m^2$ to 450 $\mu m^2$ in a cross section orthogonal to an axial direction between said distal end opening and said proximal end of the air discharge passage, and a length of the air discharge passage between said distal end opening and said proximal end is 1.0 to 3.0 mm.

* * * * *